United States Patent [19]

Jennings et al.

[11] Patent Number: 5,362,883
[45] Date of Patent: Nov. 8, 1994

[54] PROCESS FOR CYCLIC AMINO ACID ANTICONVULSANT COMPOUNDS

[75] Inventors: Rex A. Jennings, Holland; Don R. Johnson, Pinckney; Ronald E. Seamans; James R. Zeller, both of Holland, all of Mich.

[73] Assignee: Warner-Lambert Company, Morris Plains, N.J.

[21] Appl. No.: 208,771

[22] Filed: Mar. 8, 1994

Related U.S. Application Data

[60] Division of Ser. No. 72,212, Jun. 4, 1993, which is a continuation-in-part of Ser. No. 846,509, Mar. 6, 1992, which is a division of Ser. No. 564,623, Aug. 10, 1990, Pat. No. 5,132,451, which is a continuation-in-part of Ser. No. 399,056, Aug. 25, 1989, abandoned.

[51] Int. Cl.$^5$ ............................................. C07D 209/54
[52] U.S. Cl. ..................................................... 548/408
[58] Field of Search ........................................ 548/408

[56] References Cited

U.S. PATENT DOCUMENTS

| | | | |
|---|---|---|---|
| 4,024,176 | 5/1977 | Satzinger et al. | 562/507 |
| 4,087,544 | 5/1978 | Satzinger et al. | 562/507 |
| 4,152,326 | 5/1979 | Hartenstein et al. | 562/507 |
| 4,226,802 | 10/1980 | Anderson et al. | 560/43 X |
| 5,132,451 | 7/1992 | Jennings et al. | 562/507 |

FOREIGN PATENT DOCUMENTS

| | | |
|---|---|---|
| 2460891 | 7/1976 | Germany . |
| 2557220 | 6/1977 | Germany . |
| 444146 | 9/1967 | Switzerland . |

OTHER PUBLICATIONS

Justin Liebigs Annalen Der Chemie, vol. 688 (1965), pp. 113–121.

*Primary Examiner*—Joseph Paul Brust
*Attorney, Agent, or Firm*—Francis J. Tinney

[57] ABSTRACT

An improved process for the preparation of cyclic amino acids by a novel synthesis is described where a dinitrile derivative is converted in two steps to the desired products, as well as valuable intermediates used in the process.

3 Claims, No Drawings

PROCESS FOR CYCLIC AMINO ACID ANTICONVULSANT COMPOUNDS

CROSS-REFERENCE TO RELATED APPLICATION

This is a divisional application of U.S. patent application Ser. No. 08/072,212 filed Jun. 4, 1993, now allowed, which is a continuation-in-part application of U.S. patent application Ser. No. 07/846,509 filed Mar. 6, 1992, now pending, which is a divisional application of U.S. patent application Ser. No. 07/564,623, filed Aug. 10, 1990, now U.S. Pat. No. 5,132,451, which is a continuation-in-part application of U.S. patent application Ser. No. 07/399,056, filed Aug. 25, 1989, now abandoned.

BACKGROUND OF THE INVENTION

U.S. Pat. Nos. 4,024,175 and 4,087,544, which are herein incorporated by reference, disclose novel cyclic amino acids of Formula A

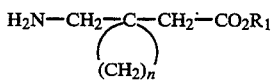

wherein $R_1$ is a hydrogen atom or a lower alkyl radical and n is 4, 5, or 6 and the pharmacologically compatible salts thereof.

The compounds disclosed in the above U.S. patents are useful for the therapy of certain cerebral diseases, for example, they can be used for the treatment of certain forms of epilepsy, faintness attacks, hypokinesia, and cranial traumas. Additionally, they bring about an improvement of cerebral functions and thus are useful in treating geriatric patients. Particularly valuable is 1-(aminomethyl)-cyclohexaneacetic acid (gabapentin).

Gamma-aminobutyric acid (GABA) is an inhibitory amino acid found in the mammalian central nervous system (CNS). It has been reported that dysfunction with GABA neurotransmission in the CNS may contribute or even cause psychiatric and neurological diseases, such as epilepsy, schizophrenia, Parkinson's disease, Huntington's Chorea, and dyskinesia (Saletu, B, et al, *International Journal of Clinical Pharmacology, Therapy and Toxicology*, 24, pages 362 to 373 (1986)). Gabapentin was designed as a GABA analog that would cross the blood-brain barrier. Gabapentin was found to have anticonvulsant and antispastic activity with extremely low toxicity in man.

The aforementioned compounds of Formula A including gabapentin have been prepared, from a compound of formula

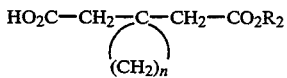

wherein $R_2$ is an alkyl radical containing up to eight carbon atoms and n is as defined above, by well known standard reactions such as, for example, the Hofmann, Curtius, or Lossen rearrangements, into the amino derivatives of Formula A. Although these reactions provide the target compounds they require a large number of synthetic steps and in some cases involve potentially explosive intermediates.

U.S. Pat. No. 4,152,326 discloses cyclic sulphonyloxyimides of formula

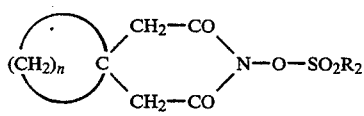

wherein $R_2$ is a saturated, straight-chained, branched or cyclic lower aliphatic radical or an unsubstituted or substituted aryl radical and n is 4, 5, or 6 which can be converted into a compound of Formula A. Again, similar to the previous processes, this process requires a large number of synthetic steps to obtain a compound of Formula A.

The object of the present invention is an improved process for preparing the compounds described above by using a novel synthesis. The particularly valuable gabapentin can be prepared in fewer steps and higher yields than the previous methods. Moreover, the present method proceeds from inexpensive starting materials and is amenable to large-scale synthesis.

SUMMARY OF THE INVENTION

Accordingly, a first aspect of the present invention is an improved process for the preparation of a compound of Formula I

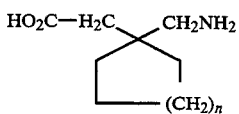

and pharmaceutically acceptable salts thereof wherein n is an integer of one to three, which comprises:

Step (a)

(1) reacting a compound of Formula V

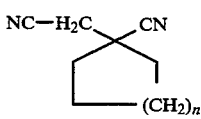

wherein n is as defined above with a compound of formula

R—OH wherein R is alkyl of from one to six carbon atoms, in a solvent, and an acid to afford in situ, after removal of excess acid a compound of Formula IV

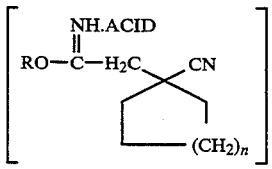

wherein n and R are as defined above;

(2) adding water and then adjusting the pH with an aqueous base, adding a water immiscible solvent, and removing the aqueous phase to afford in situ a compound of Formula III

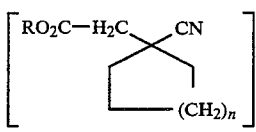

wherein n and R are as defined above;

(3) adding a phase transfer agent and an aqueous base in situ to a compound of Formula III, stirring, removing the water immiscible solvent, and adding an equivalent of an acid to afford a compound of Formula IIa

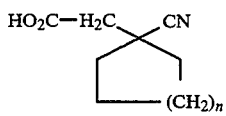

wherein n is defined as above; or treating a compound of Formula IIa with an alkali metal alkoxide, alkaline-earth metal alkoxide, ammonia, or an amine in the presence of solvent to afford a compound of Formula IIb

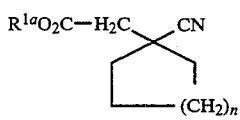

wherein $R^{1a}$ is an alkali metal, alkaline-earth metal, ammonium, or amine cation and n is as defined above;
Step (b)

treating a compound of Formula IIa or Formula IIb with hydrogen in the presence of a catalyst and a solvent to afford a compound of Formula I; or alternatively, after removing the water immiscible solvent in step (a)(3) treating in situ a compound of Formula VII

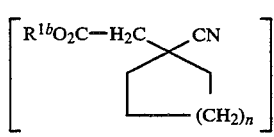

wherein $R^{1b}$ is an alkali metal or alkaline-earth metal and n is as defined above with hydrogen in the presence of a catalyst to afford a compound of Formula I;
Step (c)

and if desired, converting the resulting compound of Formula I to a corresponding pharmaceutically acceptable salt by conventional means, and if so desired, converting the corresponding pharmaceutically acceptable salt to a compound of Formula I by conventional means.

A second aspect of the present invention is an improved process for the preparation of a compound of Formula I.

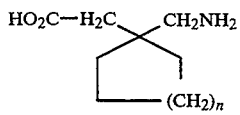

and pharmaceutically acceptable salts thereof wherein n is an integer of one to three, which comprises:
Step (a)

reacting a compound of Formula V

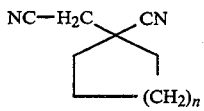

wherein n is as defined above with a compound of Formula

R—OH wherein R is alkyl of from one to six carbon atoms, in a solvent and an acid to afford in situ, after removal of excess acid, a compound of Formula IV

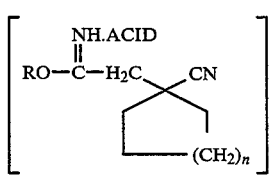

wherein n and R are as defined above;
Step (b)

adding water and then adjusting the pH with an aqueous base, adding a water immiscible solvent, and removing the aqueous phase to afford, after removal of the water immiscible solvent, a compound of Formula III

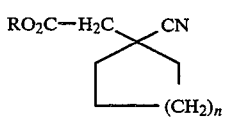

wherein n and R are as defined above;
Step (c)

treating a compound of Formula III with hydrogen in the presence of a catalyst and a solvent to afford a compound of Formula VI

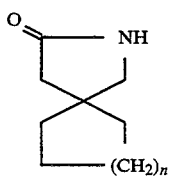

wherein n is as defined above;
Step (d)

hydrolyzing a compound of Formula VI with an acid to afford a salt of a compound of Formula I;
Step (e)

and converting the salt of a compound of Formula I to a compound of Formula I by neutralization with a base and, if desired, converting the resulting compound of Formula I to a corresponding pharmaceutically acceptable salt by conventional means.

A third aspect of the present invention is an improved process for the preparation of a compound of Formula III

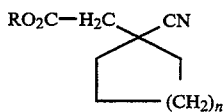 III wherein R is alkyl of from one to six carbon atoms and n is an integer of one to three which comprises:
Step (a)
reacting a compound of Formula V

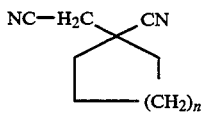 V wherein n is as defined above with a compound of formula

R—OH wherein R is as defined above, in a solvent and an acid to afford, in situ, after removal of excess acid, a compound of Formula IV

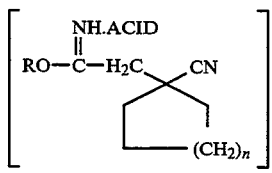 IV wherein n and R are as defined above;
Step (b)
adding water and then adjusting the pH with an aqueous base, adding a water immiscible solvent and removing the aqueous phase to afford, after removal of the water immiscible solvent a compound of Formula III.

A fourth aspect of the present invention is an improved process for the preparation of a compound of Formula II

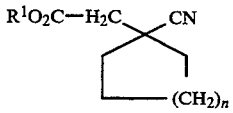 II wherein $R^1$ is hydrogen, an alkali metal, an alkaline-earth metal, ammonium, or amine cation and n is an integer of one to three, which comprises:
Step (a)
(1) reacting a compound of Formula V

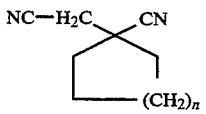 V wherein n is as defined above with a compound of formula

R—OH wherein R is alkyl of from one to six carbon atoms, in a solvent and an acid to afford in situ, after removal of excess acid, a compound of Formula IV

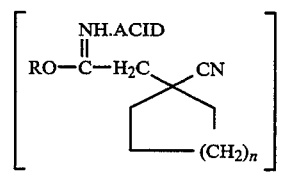 IV wherein n and R are as defined above;
(2) adding water and then adjusting the pH with an aqueous base, adding a water immiscible solvent and removing the aqueous phase to afford in situ a compound of Formula III

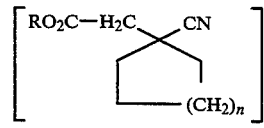 III wherein n and R are as defined above;
(3) adding a phase transfer agent and an aqueous base in situ to a compound of Formula III, stirring, removing the water immiscible solvent and adding an equivalent of an acid to afford a compound of Formula IIa

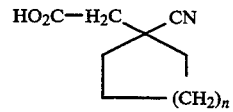 IIa wherein n is as defined above;
(4) treating a compound of Formula IIa with an alkali metal alkoxide, alkaline-earth metal alkoxide, ammonia, or an amine in the presence of a solvent to afford a compound of Formula IIb

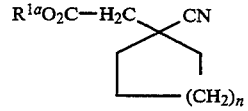 IIb wherein $R^{1a}$ is an alkali metal, alkaline-earth metal, ammonium, or amine cation and n is as defined above.

A fifth aspect of the present invention is an improved process for the preparation of a compound of Formula VI

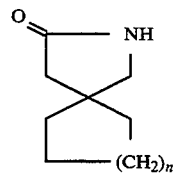 VI wherein n is an integer of one to three which comprises:
Step (a)
reacting a compound of Formula V

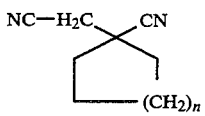

wherein n is as defined above with a compound of formula

R—OH wherein R is alkyl of from one to six carbon atoms, in a solvent and an acid to afford in situ, after removal of excess acid, a compound of Formula IV

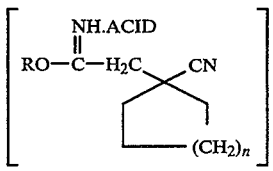

wherein n and R are as defined above;
Step (b)
adding water and then adjusting the pH with an aqueous base, adding a water immiscible solvent and removing the aqueous phase to afford, after removal of the water immiscible solvent, a compound of Formula III

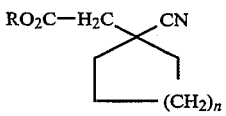

wherein n and R are as defined above;
Step (c)
treating a compound of Formula III with hydrogen in the presence of a catalyst and a solvent to afford a compound of Formula VI.

A sixth aspect of the present invention is a novel intermediate of formula

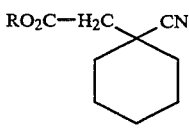

wherein R is alkyl of one to twelve carbon atoms, which is useful in the preparation of a compound of Formula I.

A seventh aspect of the present invention is a novel intermediate of formula

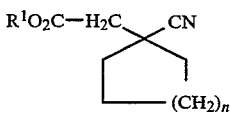

wherein $R^1$ is hydrogen, an alkali metal, an alkaline-earth metal, ammonium, or amine cation and n is an integer of one to three, which is useful in the preparation of a compound of Formula I.

DETAILED DESCRIPTION OF THE INVENTION

In this invention, the term "alkyl" means a straight or branched hydrocarbon group having from one to twelve carbon atoms and includes, for example, methyl, ethyl, n-propyl, isopropyl, n-butyl, isobutyl, tertiary-butyl, n-pentyl, n-hexyl, n-heptyl, n-octyl, n-nonyl, n-decyl, undecyl, dodecyl, and the like.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

"Phase transfer agent" means a solvent which is mutually soluble in the aqueous phase and organic phase and includes, for example, methanol, ethanol, isopropanol, tetrahydrofuran, dioxane, and the like.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Pharmaceutically acceptable base addition salts are formed with metals or amines, such as alkali and alkaline earth metals or organic amines. Examples of metals used as cations are sodium, potassium, magnesium, calcium and the like. Examples of suitable amines are N,N'-dibenzylethylenediamine, chloroprocaine, choline, diethanolamine, ethylenediamine, N-methylglucamine, and procaine (see, for example, Berge, S. M., et al., "Pharmaceutical Salts," *Journal of Pharmaceutical Science*, 66, pp. 1-19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acids for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

U.S. patent application Ser. No. 07/188,819, now U.S. Pat. No. 4,894,476, discloses gabapentin monohydrate and a process for producing the gabapentin monohydrate.

A preferred compound of Formula I prepared by the improved process of the first aspect of the present invention is:
  1-(aminomethyl)-cyclohexaneacetic acid A preferred compound of Formula I prepared by the improved process of the second aspect of the present invention is:
  1-(aminomethyl)-cyclohexaneacetic acid A preferred compound of Formula III prepared by the improved process of the third aspect of the present invention is:

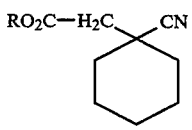

wherein R is alkyl of from one to six carbon atoms.

Preferred compounds of Formula II prepared by the improved process of the fourth aspect of the present invention are:
  1-cyanocyclohexaneacetic acid; sodium 1-cyanocyclohexaneacetate; and potassium 1-cyanocyclohexaneacetate.

A preferred compound of Formula VI prepared by the improved process of the fifth aspect of the present invention is:
  2-azaspiro[4.5]decan-3-one.

A preferred novel intermediate of the sixth aspect of the present invention are:
  ethyl 1-cyanocyclohexaneacetate.

Preferred novel intermediates of the seventh aspect of the present invention are:
  1-cyanocyclohexaneacetic acid; sodium 1-cyanocyclohexaneacetate; and potassium 1-cyanocyclohexaneacetate.

As previously described, the compounds of Formula I are useful for the treatment of certain forms of epilepsy, faintness attacks, hypokinesia, and cranial traumas.

The process of the present invention in its first aspect is a new, improved, economical, and commercially feasible method for preparing a compound of Formula I. Furthermore, the process can be carried out in a two-pot procedure requiring only isolation of the penultimate intermediate and the final product. The process of the present invention in its first aspect is outlined in Scheme I:

SCHEME I

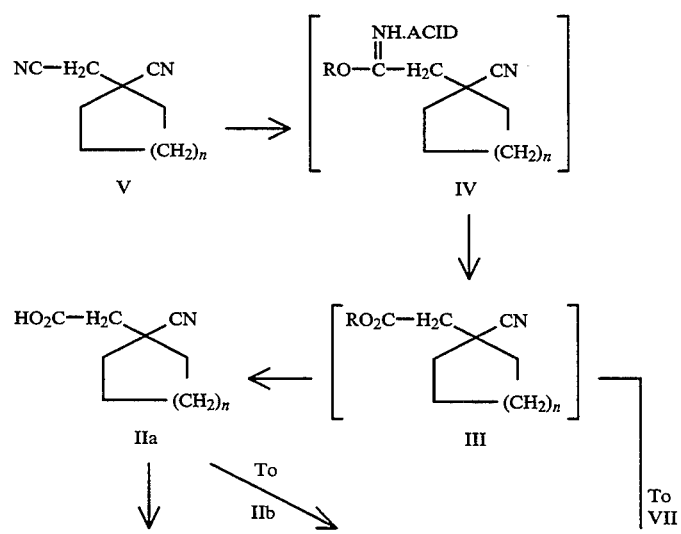

SCHEME I

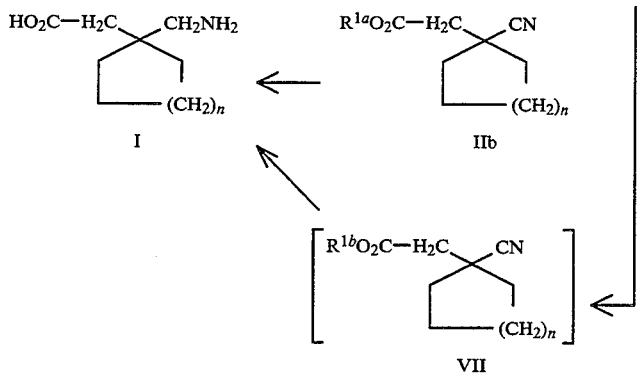

A compound of Formula IIa is prepared from a known dinitrile of Formula V.

In the preparation of a series of α,α-disubstituted succinimides via cyano imidoester intermediates Schafer, H. (Liebigs Annalen der Chemie, 668, pages 113 to 121 (1965)) reported "a special stability" to hydrolysis of the cyano imidoesters to cyano esters. We have unexpectedly and surprisingly found that by removing excess acid after formation of the cyano imidoester in situ in the present process that hydrolysis in situ to the cyano ester proceeds smoothly and with negligible formation of succinimide by-product.

Thus, a compound of Formula V, wherein n is an integer of one to three is treated with about one equivalent of a compound of formula

R—OH wherein R is alkyl of from one to six carbon atoms, for about one to five days in a solvent such as, for example, toluene, ethyl acetate, methylene chloride, ethanol, methanol, and the like and about one to three equivalents of an inorganic or organic acid such as, for example, hydrochloric acid, hydrobromic acid, sulfuric acid, methanesulfonic acid, trifluoroacetic acid, and the like at a pressure of about 2 mm to about 50 pounds per square inch gauge (psig) and about −20° C. to about 55° C. to afford, after removal of excess acid, a compound of Formula IV wherein n and R are as defined above which is not isolated. Preferably the reaction is carried out by adding about two equivalents of anhydrous hydrogen chloride at a pressure of about 3 mm to about 10 mm Hg and about 10° C. to an evacuated flask containing the dinitrile of Formula V in toluene containing about 2 equivalents of ethanol or methanol, stirring for two days and removing excess acid by distillation.

Water is added and the pH is adjusted to about 1 to about 4.5 with an aqueous base such as, for example, an aqueous alkali or alkaline earth-metal hydroxide or carbonate, for example, sodium hydroxide, potassium hydroxide, calcium hydroxide, sodium carbonate, potassium carbonate, calcium carbonate, and the like. The mixture is stirred for about one to about 36 hours at about 0° C. to about 50° C. and a water immiscible solvent such as, for example, toluene, ethyl acetate, methylene chloride, hexane, heptane, octane, isooctane, tertiary butyl methyl ether, and the like is added to afford, after removal of the aqueous phase, a compound of Formula III wherein n and R are as defined above, which is not isolated. Preferably the reaction is carried out by adjusting the pH to about 4 to about 4.5 with aqueous sodium hydroxide, stirring for about 24 hours, and adding toluene.

A phase transfer agent such as, for example, methanol, ethanol, isopropanol, tetrahydrofuran, dioxane, and the like, and an aqueous base such as, for example, an aqueous alkali or alkaline earth-metal hydroxide or carbonate, for example, sodium hydroxide, potassium hydroxide, calcium hydroxide, sodium carbonate, potassium carbonate, calcium carbonate and the like are added to the previous water immiscible solvent containing a compound of Formula III and stirring is continued for about five minutes to about five hours at about 0° C. to about the reflux temperature of the solvent. The water immiscible solvent is removed and an equivalent of an inorganic or organic acid such as, for example, hydrochloric acid, hydrobromic acid, sulfuric acid, trifluoroacetic acid and the like is added to afford a compound of Formula II wherein n is as defined above. Preferably the reaction is carried out in methanol and aqueous sodium hydroxide for about four hours at about 40° C., removing the toluene and adding an equivalent of concentrated hydrochloric acid at about 0° C. to about 5° C.

A compound of Formula IIa is treated with hydrogen in the presence of a catalyst such as, for example, rhodium on carbon containing palladium, rhodium on carbon containing platinum, rhodium on calcium carbonate containing palladium, rhodium on alumina containing palladium, palladium on carbon, palladium on carbon in the presence of a mineral acid such as, for example, hydrochloric acid, sulfuric acid, phosphoric acid, and the like, Raney nickel, Raney nickel and a base such as, for example, an alkali metal hydroxide, ammonium hydroxide and the like, Raney cobalt, metal hydrides such as, for example, lithium aluminum hydride, rhodium hydrido complex, ruthenium hydrido complex, borane methyl sulfide complex and the like, and metals such as, for example, iron, cobalt, nickel, rhodium, and the like in a solvent such as, for example, methanol, ethanol, 1-propanol, 2-propanol, 1-butanol, 2-butanol, and the like at about −20° C. to about 50° C. to afford a compound of Formula I wherein n is as defined above. Preferably the reaction is carried out with 0.5% to 10% rhodium on carbon containing 1% to 10% palladium in methanol at about room temperature.

Additionally, a compound of Formula IIa is treated with an alkali metal alkoxide such as, for example, sodium methoxide, sodium ethoxide, potassium methoxide, potassium ethoxide, potassium tertiary butoxide, and the like, an alkaline-earth metal alkoxide such as, for example, magnesium ethoxide, and the like, ammonia, an amine capable of forming a salt with a carboxylic, acid such as, for example, triethylamine, pyridine, and the like in the presence of a solvent such as, for example, tetrahydrofuran, and the like to afford a compound of Formula IIb. Preferably the reaction is carried out with sodium methoxide or potassium tertiary butoxide in tetrahydrofuran. A compound of Formula IIb is converted to a compound of Formula I using the methodology previously described for preparing a compound of Formula I from a compound of Formula IIa.

Additionally, a phase transfer agent and an aqueous base are added to the water immiscible solvent containing a compound of Formula III as previously described. The water immiscible solvent is removed and a compound of Formula VII wherein $R^{1b}$ is an alkali metal or alkaline-earth metal and n is as defined above is converted in situ to a compound of Formula I using the methodology previously described for preparing a compound of Formula I from a compound of Formula IIa or Formula IIb.

The process of the present invention in its second aspect is a new, improved, economical and commercially feasible method for preparing a compound of Formula I. The process of the present invention in its second aspect is outlined in Scheme II.

Thus a compound of Formula V is converted into a compound of Formula III as previously described.

A compound of Formula III is isolated and treated with hydrogen in the presence of a catalyst using the methodology previously described for preparing a compound of Formula I from a compound of Formula IIa or Formula IIb to afford a compound of Formula VI wherein n is as defined above. Preferably, the reaction is carried out with sponge nickel catalyst in 2-propanol.

A compound of Formula VI is converted to a salt of a compound of Formula I by acid hydrolysis such as, for example, acid hydrolysis with hydrochloric acid, sulfuric acid and the like, and subsequently converted to a compound of Formula I by neutralization of the acid addition salt such as, for example, treatment with a base such as, for example, an alkali or alkaline earth-metal hydroxide or carbonate, for example, sodium hydroxide, potassium hydroxide, calcium hydroxide, sodium carbamate, potassium carbamate, calcium carbamate, and the like or an amine, for example, triethylamine, pyridine, and the like or ion exchange techniques. Preferably, neutralization is carried out with a basic ion exchange resin. Additionally, in the first aspect of the invention any formed by-product of Formula VI may be converted as previously described to a compound of Formula I.

A compound of Formula V may be prepared by methodology described by Schafer, H., *Liebigs Annalen der Chemie*, 688, pp 113 to 121 (1965).

The following nonlimiting example illustrates the inventors' preferred method for preparing the compounds of the invention.

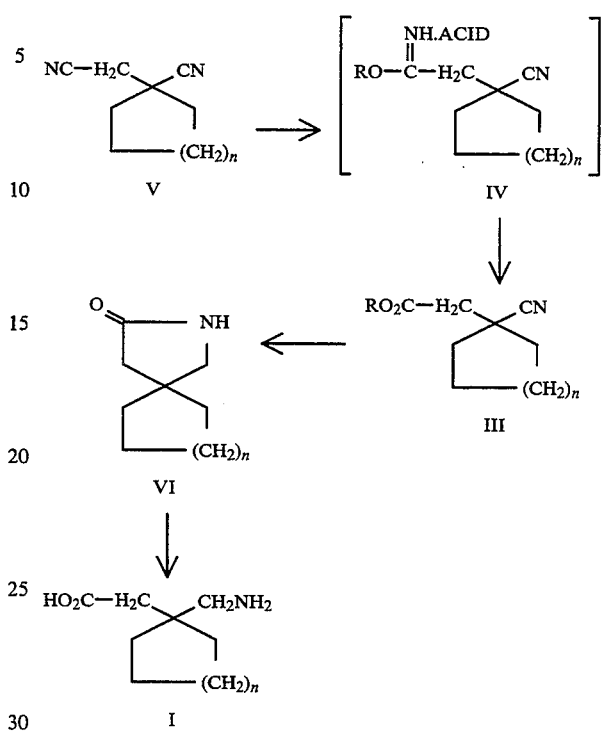

SCHEME II

EXAMPLE 1

1-(Aminomethyl)-cyclohexaneacetic Acid

METHOD A

Step A: Preparation of 1-Cyanocyclohexaneacetic Acid

A 2-liter flask is charged with 242 g (1.63 mol) of 1-cyanocyclohexaneacetonitrile, 150 g of ethanol, and 536 ml of toluene. The flask is cooled to 10° C. and evacuated. Anhydrous hydrogen chloride (159 g, 4.35 mol) is added to the evacuated flask, causing the pressure to rise to ambient. The mixture is held cold for three days, at which point an additional 40 g of hydrogen chloride gas is added. The mixture is stirred cold for an additional four days, at which point the solvent and excess hydrogen chloride are removed by distillation under vacuum, maintaining the flask at below 25° C. The mixture is cooled in an ice bath and 1500 ml of water is added over a 30-minute period. Aqueous sodium hydroxide is added to raise the pH to 4 to 4.5. This mixture is stirred for 24 hours, and then 300 ml of toluene is added. The aqueous phase is removed, and 100 ml of methanol and 600 ml of 3 M sodium hydroxide are added to the toluene phase. The mixture is warmed to 40° C. and stirred for four hours. The toluene phase is removed and the aqueous phase is cooled to 0° to 5° C., then the pH of the aqueous phase is adjusted to 3 with concentrated hydrochloric acid with stirring at 0° to 5° C., and filtered. The filter cake is dried to give 212.5 g (78% of theory) of white crystalline 1-cyanocyclohexaneacetic acid; mp 102°–103° C.

Step B: Preparation of 1-(Aminomethyl)-cyclohexaneacetic Acid

One gram of 10% rhodium on carbon, containing 1% palladium, (Pearlman, W. M., *Tetrahedron Letters*, pages 1663–1664 (1967)) is slurried in 30 ml methanol and reduced under hydrogen in a Parr shaker. 1-

Cyanocyclohexaneacetic acid (16.7 g, 0.1 mol) is dissolved in 40 ml methanol and combined with the reduced catalyst. The mixture is placed under 50 pounds per square inch gauge (psig) hydrogen and shaken for two hours at room temperature. The catalyst is removed by filtration, and the filtrate is condensed to a volume of 25 ml by vacuum distillation. Isopropanol, 100 ml, is added and an additional 25 to 50 ml of solvent is removed by vacuum distillation. The resultant slurry is cooled at 0° to 5° C. for 24 hours and filtered and dried to give 13.65 g (79% of theory) of 1-(aminomethyl)-cyclohexaneacetic acid; mp 162°–163° C.

METHOD B

To a 500-mL Parr bomb is added 23.5 g (0.1 mol) of 1-cyanocyclohexaneacetic acid, 28% water wet; 16 g of 50% water wet Raney nickel #30, and a cooled (20° C.) methyl alcohol (160 mL) and 50% aqueous sodium hydroxide (8.8 g, 0.11 mol) solution. The reaction mixture is stirred at 22° C. to 25° C. for 21 hours at 180 pounds per square inch gauge (psig) hydrogen. After 21 hours, the hydrogen is vented and the reduced mixture is flushed with nitrogen.

The reaction mixture is pressure filtered over celite, washed with methyl alcohol (100 mL), and stripped to a volume of 50 mL at 35° C. on the rotary evaporator. Isopropyl alcohol (100 mL) is added followed by the dropwise addition of 6.6 g (0.11 mol) of acetic acid. The product solution is stripped on the rotary evaporator to a volume of 50 mL. Tetrahydrofuran (125 mL) is added to the concentrated product solution, the solution cooled in an ice bath, suction filtered, and washed using 50 mL of tetrahydrofuran. The crude product cake is dried under vacuum at 45° C. for 16 hours.

The crude product is recrystallized from methyl alcohol, demineralized water, and isopropyl alcohol to yield 10.3 g of 1-(aminomethyl)-cyclohexaneacetic acid as a crystalline white solid. The high-performance liquid chromatography (HPLC) results show no organic impurities detected with a 97.2% weight/weight (w/w) purity.

METHOD C

Step A Preparation of Ethyl 1-cyanocyclohexaneacetate

A 1-L pressure flask is charged with 148 g (1 mol) of 1-cyanocyclohexaneacetonitrile, 206 mL of ethanol, and 100 mL of toluene. The mixture is cooled to 5° C. and evacuated. Anhydrous hydrogen chloride (148 g, 4.05 mol) is added to the evacuated flask, causing the pressure to rise to 10 pounds per square inch gauge (psig) while allowing the temperature to rise to 35° C. This temperature is maintained for 7 hours, during which time additional hydrogen chloride (25 g, 0.68 mol) is added to maintain a pressure of 5 pounds per square inch gauge (psig). At the end of the 7-hour period, the excess hydrogen chloride and ethanol are removed by vacuum distillation, maintaining the mixture at below 25° C. To the resulting slurry is added 200 mL of toluene, which is then removed by vacuum distillation. This procedure is repeated two more times with 150 mL of toluene. After the final distillation, 150 mL of toluene and 500 mL of ice water are added and the pH adjusted to four with aqueous sodium hydroxide solution. After stirring for 18 hours, the mixture is filtered, the filtrate layers separated, the aqueous layer washed with 100 mL of toluene, and then the combined toluene layers washed with 100 mL of 1N aqueous sodium hydroxide solution, followed by two water washes of 50 mL each. The toluene solution is then dried by azeotropic distillation, which is followed by vacuum distillation to remove the toluene. The residual yellow oil (166 g) is 91% ethyl 1-cyanocyclohexaneacetate. Further purification can be effected by vacuum distillation, collecting distillate with bp 85° to 95° C. at 0.2 to 0.3 mm of Hg.

Step B: Preparation of 1-Cyanocyclohexaneacetic Acid

To a suitable reactor is charged 120 L of water, 32 kg of 50% aqueous sodium hydroxide solution, 21 L of methanol, and 70 kg of ethyl 1-cyanocyclohexaneacetate. This mixture is stirred at 50° C. for 1 hour, after which 40 to 60 L of solvent is removed by vacuum distillation while maintaining a temperature of below 50° C. After cooling to 20° to 25° C., the reaction mixture is filtered through a 0.45 micron Pall filter. The filtered solution is then diluted with 70 L of water and extracted with 20 L of methylene chloride, followed by a second extraction with 15 L of methylene chloride. The aqueous solution is charged to a pH of 8 with 37% hydrochloric acid solution. About 6 to 8 kg of 37% hydrochloric acid solution is required. The solution is then extracted two times with 20 L each of methylene chloride. After the final extraction, the aqueous solution is stirred under full vacuum at 20° to 30° C. for 30 minutes minimum, then cooled to 3° to 10° C. While maintaining this temperature, 37% hydrochloric acid solution is charged to a pH of 3. About 32 to 36 kg of 37% hydrochloric acid solution is required. After the addition is complete, the product slurry is stirred at 3° to 10° C. for 30 minutes. The product is then collected on a centrifuge and washed with 300 to 400 L of water which is prechilled to 5° C. or less. The product is spun as dry as possible on the centrifuge and is then removed from the centrifuge and stored as a wet cake in a cold room at 5° C. or less. After vacuum drying at 40° C. for 24 hours 1-cyanocyclohexaneacetic acid is obtained; mp 103°–105° C.

Step C: Preparation of 1-(Aminomethyl)-cyclohexaneacetic Acid

Using the procedure of Method B 1-cyanocyclohexaneacetic acid is converted to 1-(aminomethyl)-cyclohexaneacetic acid.

METHOD D

Step A: Preparation of Sodium 1-cyanocyclohexaneacetate

To a 250-mL flask under nitrogen is added 7.1 g (0.13 mol) of sodium methoxide followed by 20 mL of methyl alcohol and 270 mL of tetrahydrofuran. The solution is suction filtered over celite and washed using 10 mL of tetrahydrofuran. The filtrates are combined and transferred into an addition funnel and a 500-mL flask containing 20 g of 1-cyanocyclohexaneacetic acid and 100 mL of tetrahydrofuran. The sodium methoxide solution is added over 3 minutes to the previous solution. The precipitated product is cooled in an ice bath, suction filtered, and washed using 20 mL of tetrahydrofuran. The filter cake is dried in a vacuum oven at 50° C. for 16 hours to give 21.9 g of sodium 1-cyanocyclohexaneacetate as an off-white crystalline solid; mp 206°–209° C.

Step B: Preparation of 1-(Aminomethyl)-cyclohexaneacetic Acid

Using the procedure of Method B, sodium 1-cyanocyclohexaneacetate is converted to 1-(aminomethyl)-cyclohexaneacetic acid.

METHOD E

Step A: Preparation of Potassium 1-cyanocyclohexaneacetate

To a 250-mL flask under nitrogen is added 14.8 g (0.13 mol) of potassium tertiary butoxide followed by 74 mL of tetrahydrofuran. The solution is stirred for 10 minutes, suction filtered, and washed using 50 mL of tetrahydrofuran. The filtrates are combined and transferred into an addition funnel on a separate 250-mL flask containing 20 g (0.12 mol) of dried 1-cyanocyclohexaneacetic acid and 100 mL of tetrahydrofuran. The potassium tertiary butoxide solution is added dropwise over 5 minutes to the previous solution. The precipitate is cooled in an ice bath, suction filtered, and washed with 25 mL of cold tetrahydrofuran. The filter cake is dried in a vacuum oven at 50° C. for 16 hours to give 24.8 g of potassium 1-cyanocyclohexaneacetate as a white crystalline solid; mp 196°-199° C.

Step B: Preparation Of 1-(Aminomethyl)-cyclohexaneacetic Acid

Using the procedure of Method B, potassium 1-cyanocyclohexaneacetate is converted to 1-(aminomethyl)-cyclohexaneacetic acid.

METHOD F
Step A: Preparation of 2-Azaspiro[4.5]decan-3-one

Ethyl 1-cyanocyclohexaneacetate (29.3 g) is combined with isopropanol (75 mL) and sponge nickel catalyst (6 g, 50% water wet) and hydrogenated at 300 psig at 130° C. The reaction mixture is cooled and the catalyst is removed by filtration, and the liquors are concentrated. The lactam product can be isolated as a white solid, if desired, by the addition of heptane (150 mL) followed by filtration (yield 18.6 g, 81%).

Step B: Preparation Of 1-(Aminomethyl)-cyclohexaneacetic Acid

An isopropanol solution of 2-azaspiro[4.5]decan-3-one from Step A, after catalyst filtration (363 g of an 11% solution) is concentrated by distillation. To the concentrate (or 40 g isolated solid lactam product, if desired) is added 52 g of 37% hydrochloric acid and 44 g of water and the mixture is refluxed for 12 to 18 hours. The resultant solution is cooled and extracted with toluene. The aqueous fraction is passed through a basic ion exchange column to neutralize the acid. The eluent is concentrated and treated with isopropanol to precipitate 1-(aminomethyl)-cyclohexaneacetic acid, hydrate. The hydrate is then slurried in isopropanol and methanol (60 mL each) at 45° C. for 5 hours to convert from the hydrate to the anhydrous form. The slurry is filtered to give 25.6 g (56% yield) of 1-(aminomethyl)-cyclohexaneacetic acid. The toluene extracts and the 1-(aminomethyl)-cyclohexaneacetic acid, hydrate filtrates are combined and concentrated, and the resultant mixture is recycled in the next hydrolysis reaction. The subsequent hydrolysis reactions, which include the recycle streams, achieve a steady-state yield for the hydrolysis reaction of 85%.

We claim:

1. A process for the preparation of a compound of Formula VI

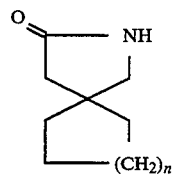

wherein n is an integer of one to three which comprises:
Step (a)
reacting a compound of Formula V

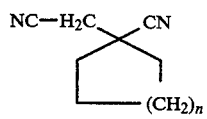

wherein n is as defined above with a compound of formula

R—OH wherein R is alkyl of from one to six carbon atoms, in a solvent and an acid to afford in situ, after removal of excess acid, a compound of Formula IV

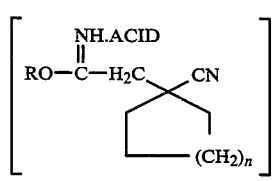

wherein n and R are as defined above;
Step (b)
adding water and then adjusting the pH with an aqueous base, adding a water immiscible solvent and removing the aqueous phase to afford, after removal of the water immiscible solvent, a compound of Formula III

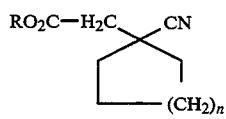

wherein n and R are as defined above;
Step (C)
treating a compound of Formula III with hydrogen in the presence of a catalyst and a solvent to afford a compound of Formula VI.

2. A process according to claim 1 wherein the pH in Step (b) is adjusted to about 1 to about 4.5.

3. A process according to claim 1 for the preparation of 2-azaspiro[4.5]decan-3-one.

* * * * *